US010100033B2

(12) United States Patent
Li et al.

(10) Patent No.: US 10,100,033 B2
(45) Date of Patent: Oct. 16, 2018

(54) PROCESSES FOR THE PREPARATION OF PESTICIDAL COMPOUNDS

(71) Applicant: Dow AgroSciences LLC, Indianapolis, IN (US)

(72) Inventors: Xiaoyong Li, Midland, MI (US); Erich Molitor, Midland, MI (US); Gary Alan Roth, Midland, MI (US); Matthias S. Ober, Midland, MI (US); Patrick Hanley, Midland, MI (US); Tina T. Staton, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/853,096

(22) Filed: Dec. 22, 2017

(65) Prior Publication Data
US 2018/0186766 A1 Jul. 5, 2018

Related U.S. Application Data

(60) Provisional application No. 62/440,232, filed on Dec. 29, 2016.

(51) Int. Cl.
*C07D 401/04* (2006.01)
*A01N 43/56* (2006.01)

(52) U.S. Cl.
CPC ........... *C07D 401/04* (2013.01); *A01N 43/56* (2013.01)

(58) Field of Classification Search
CPC .................................................... C07D 401/04
USPC ...................................................... 546/275.4
See application file for complete search history.

(56) References Cited

U.S. PATENT DOCUMENTS

| 3,597,341 A | 8/1971 | Oswald |
| 4,080,457 A | 3/1978 | Harrison et al. |
| 4,260,765 A | 4/1981 | Harrison et al. |
| 4,347,251 A | 8/1982 | Joseph et al. |
| 4,407,803 A | 10/1983 | Haviv et al. |
| 4,536,506 A | 8/1985 | Marcoux et al. |
| 4,556,671 A | 12/1985 | Copp et al. |
| 4,734,125 A | 3/1988 | Gehring et al. |
| 4,810,719 A | 3/1989 | Appleton et al. |
| 4,824,953 A | 4/1989 | Bronn |
| 5,220,028 A | 6/1993 | Iwasawa et al. |
| 5,625,074 A | 4/1997 | Daum et al. |
| 5,631,380 A | 5/1997 | Haas et al. |
| 5,652,372 A | 7/1997 | Muller et al. |
| 5,693,657 A | 12/1997 | Lee et al. |
| 5,750,718 A | 5/1998 | Muller et al. |
| 5,817,677 A | 10/1998 | Linz et al. |
| 5,854,264 A | 12/1998 | Anthony et al. |
| 5,854,265 A | 12/1998 | Anthony et al. |
| 5,869,681 A | 2/1999 | Muller et al. |
| 6,040,331 A | 3/2000 | Yamamoto et al. |
| 6,218,418 B1 | 4/2001 | Pevarello et al. |
| 6,413,984 B1 | 7/2002 | Philippo et al. |
| 6,506,747 B1 | 1/2003 | Betageri et al. |
| 6,548,525 B2 | 4/2003 | Galemmo, Jr. et al. |
| 6,720,427 B2 | 4/2004 | Sanner et al. |
| 6,878,196 B2 | 4/2005 | Harada et al. |
| 6,916,927 B2 | 7/2005 | Bunnage et al. |
| 6,965,032 B2 | 11/2005 | Freudenberger et al. |
| 7,192,906 B2 | 3/2007 | Hirohara et al. |
| 7,196,104 B2 | 3/2007 | Askew, Jr. et al. |
| 7,319,108 B2 | 1/2008 | Scwink et al. |
| 7,774,978 B2 | 8/2010 | Ding et al. |
| 7,803,832 B2 | 9/2010 | Critcher et al. |
| 7,910,606 B2 | 3/2011 | Nazere et al. |
| 7,923,573 B2 | 4/2011 | Tamaki et al. |
| 8,163,756 B2 | 4/2012 | Flynn et al. |
| 8,222,280 B2 | 7/2012 | Liu et al. |
| 8,815,271 B2* | 8/2014 | Yap .................... A61K 45/06 424/405 |
| 8,901,153 B2 | 12/2014 | Buysse et al. |
| 9,024,031 B1 | 5/2015 | Yang et al. |
| 9,029,554 B1 | 5/2015 | Yang et al. |
| 9,029,555 B1 | 5/2015 | Li et al. |
| 9,029,556 B1 | 5/2015 | Yang et al. |
| 9,044,017 B2 | 6/2015 | Yang et al. |
| 9,085,552 B1 | 7/2015 | Li et al. |
| 9,085,564 B2 | 7/2015 | Yang et al. |
| 9,102,654 B2 | 8/2015 | Yang et al. |
| 9,102,655 B2* | 8/2015 | Yang .................. C07C 321/14 |

(Continued)

FOREIGN PATENT DOCUMENTS

| CN | 87107798 | 5/1988 |
| CN | 1339027 | 3/2002 |

(Continued)

OTHER PUBLICATIONS

Kempe et al., "Responsive Glyco-poly(2-oxaoline)s: Synthesis, Cloud Point Tuning, and Lectin Binding," Biomacromolecules 2011, vol. 12, pp. 2591-2600.

Fields et al., "Preparation of Trifluoromethyl-Pyrazoles and -Pyrazolines by the Reaction of 2,2,2-Trifluorodiazoethane with Carbon-Carbon Multiple Bonds," Journal of Fluorine Chemistry, 1979, vol. 13, pp. 147-158.

Bradbury et al., "Enzyme-catalysed peptide amidation," Eur. J. Biochem. 1987, vol. 169, pp. 579-584.

(Continued)

*Primary Examiner* — Charanjit Aulakh

(74) *Attorney, Agent, or Firm* — Barnes & Thornburg LLP

(57) ABSTRACT

This application relates to efficient and economical synthetic chemical processes for the preparation of pesticidal thioethers and pesticidal sulfoxides. Further, the present application relates to certain novel compounds necessary for their synthesis. It would be advantageous to produce pesticidal thioethers and pesticidal sulfoxides efficiently and in high yield from commercially available starting materials.

20 Claims, No Drawings

(56) References Cited

U.S. PATENT DOCUMENTS

| | | |
|---|---|---|
| 9,108,932 B2 | 8/2015 | Ross et al. |
| 9,108,946 B2 | 8/2015 | Yang et al. |
| 9,115,115 B1 | 8/2015 | Yang et al. |
| 9,126,974 B2 | 8/2015 | Yang et al. |
| 9,156,813 B1 | 10/2015 | Li et al. |
| 9,174,962 B2 | 11/2015 | Yang et al. |
| 9,199,942 B2 | 12/2015 | Yang et al. |
| 9,199,964 B1 | 12/2015 | Yang et al. |
| 9,249,122 B1 | 2/2016 | Yang et al. |
| 9,255,081 B1 | 2/2016 | Li et al. |
| 9,255,082 B2 | 2/2016 | Yang et al. |
| 9,255,083 B2 | 2/2016 | Yang et al. |
| 9,260,396 B2 | 2/2016 | Yang et al. |
| 9,371,310 B2 | 6/2016 | Yang et al. |
| 9,414,594 B2 | 8/2016 | Yang et al. |
| 9,422,265 B2 | 8/2016 | Li et al. |
| 9,433,215 B2 | 9/2016 | Yang et al. |
| 9,434,712 B2 | 9/2016 | Yang et al. |
| 9,447,048 B2 | 9/2016 | Yang et al. |
| 9,522,900 B2 | 12/2016 | Yang et al. |
| 9,540,342 B2 * | 1/2017 | Yang .................. C07C 321/14 |
| 9,550,751 B2 | 1/2017 | Yang et al. |
| 9,573,931 B2 | 2/2017 | Yang et al. |
| 9,580,403 B2 | 2/2017 | Li et al. |
| 9,580,405 B2 | 2/2017 | Yang et al. |
| 9,604,942 B2 | 3/2017 | Ross et al. |
| 9,611,247 B2 | 4/2017 | Yang et al. |
| 9,661,849 B2 | 5/2017 | Yang et al. |
| 9,663,489 B2 | 5/2017 | Li et al. |
| 9,670,164 B2 | 6/2017 | Yang et al. |
| 9,670,178 B2 | 6/2017 | Yang et al. |
| 9,809,570 B2 | 11/2017 | Yang et al. |
| 9,840,490 B2 | 12/2017 | Li et al. |
| 9,862,702 B2 | 1/2018 | Yang et al. |
| 2002/0013326 A1 | 1/2002 | Tiebes et al. |
| 2003/0153464 A1 | 8/2003 | Nakamura et al. |
| 2003/0213405 A1 | 11/2003 | Harada et al. |
| 2004/0043904 A1 | 3/2004 | Yamaguchi et al. |
| 2004/0082629 A1 | 4/2004 | Iwataki et al. |
| 2004/0255397 A1 | 12/2004 | Fessmann et al. |
| 2005/0038059 A1 | 2/2005 | Mueller et al. |
| 2005/0176710 A1 | 8/2005 | Schwink et al. |
| 2006/0135778 A1 | 6/2006 | Schnatterer et al. |
| 2006/0160857 A1 | 7/2006 | Buettelmann et al. |
| 2006/0160875 A1 | 7/2006 | Gaines et al. |
| 2006/0167020 A1 | 7/2006 | Dickerson et al. |
| 2006/0287365 A1 | 12/2006 | Billen et al. |
| 2006/0287541 A1 | 12/2006 | Nishino et al. |
| 2007/0049604 A1 | 3/2007 | Nam et al. |
| 2007/0167426 A1 | 7/2007 | Siddiqui et al. |
| 2008/0004301 A1 | 1/2008 | Tamaki et al. |
| 2008/0027046 A1 | 1/2008 | Annan et al. |
| 2009/0023709 A1 | 1/2009 | Gillespie et al. |
| 2009/0069288 A1 | 3/2009 | Breinlinger et al. |
| 2009/0137524 A1 | 5/2009 | Billen et al. |
| 2009/0275592 A1 | 11/2009 | Zeng et al. |
| 2009/0325956 A1 | 12/2009 | Taniguchi et al. |
| 2010/0130474 A1 | 5/2010 | Bothmann et al. |
| 2010/0204164 A1 | 8/2010 | Crouse et al. |
| 2010/0286169 A1 | 11/2010 | Guiles et al. |
| 2010/0292253 A1 | 11/2010 | Trullinger et al. |
| 2010/0305200 A1 | 12/2010 | Velicelebi et al. |
| 2011/0021771 A1 | 1/2011 | Mallais et al. |
| 2011/0048261 A1 | 3/2011 | Shimura |
| 2011/0098287 A1 | 4/2011 | Bretschneider et al. |
| 2011/0118290 A1 | 5/2011 | Bretschneider et al. |
| 2011/0166129 A1 | 7/2011 | Machacek et al. |
| 2011/0166143 A1 | 7/2011 | Bretschneider et al. |
| 2011/0184188 A1 | 7/2011 | Wada et al. |
| 2011/0201649 A1 | 8/2011 | Matsuzaki et al. |
| 2011/0212949 A1 | 9/2011 | Bretschneider et al. |
| 2011/0275583 A1 | 11/2011 | Bretschneider et al. |
| 2011/0319428 A1 | 12/2011 | Fußlein et al. |
| 2012/0053146 A1 | 3/2012 | Parker et al. |
| 2012/0094837 A1 | 4/2012 | Muhlthau et al. |
| 2012/0095023 A1 | 4/2012 | Bretschneider et al. |
| 2012/0101294 A1 | 4/2012 | Hirota et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0172218 A1 | 7/2012 | Crouse et al. |
| 2012/0220453 A1 | 8/2012 | Lowe et al. |
| 2012/0252770 A1 | 10/2012 | Berger et al. |
| 2013/0019348 A1 | 1/2013 | Crouse et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1 | 10/2013 | Bretschneider et al. |
| 2013/0288893 A1 | 10/2013 | Buysse et al. |
| 2013/0291227 A1 | 10/2013 | Buysse et al. |
| 2013/0324736 A1 | 12/2013 | Ross, Jr. et al. |
| 2013/0324737 A1 | 12/2013 | Ross, Jr. et al. |
| 2013/0338367 A1 | 12/2013 | Numata et al. |
| 2014/0016287 A1 | 6/2014 | Yap et al. |
| 2014/0309446 A1 | 10/2014 | Amajjahe et al. |
| 2015/0112076 A1 | 4/2015 | Yang et al. |
| 2015/0252016 A1 | 9/2015 | Yang et al. |
| 2016/0031849 A1 | 2/2016 | Yang et al. |
| 2016/0152593 A1 | 6/2016 | Li et al. |
| 2017/0044134 A1 | 2/2017 | Yang et al. |
| 2017/0081288 A1 | 3/2017 | Yang et al. |
| 2017/0101393 A1 | 4/2017 | Li et al. |
| 2017/0215420 A1 | 8/2017 | Yang et al. |
| 2017/0217924 A1 | 8/2017 | Li et al. |
| 2017/0233367 A1 | 8/2017 | Yang et al. |
| 2017/0295786 A1 | 10/2017 | Yang et al. |

FOREIGN PATENT DOCUMENTS

| | | |
|---|---|---|
| CN | 1373662 | 10/2002 |
| CN | 1852885 A | 10/2006 |
| CN | 1307161 C | 3/2007 |
| CN | 101228134 | 7/2008 |
| EP | 0097323 | 1/1984 |
| EP | 0190457 | 8/1986 |
| EP | 0205024 | 12/1986 |
| EP | 0232538 | 8/1987 |
| EP | 0248315 | 12/1987 |
| EP | 0425948 | 5/1991 |
| EP | 0273549 | 1/1992 |
| EP | 0757987 | 4/1994 |
| EP | 1273582 | 1/2003 |
| EP | 1321463 | 6/2003 |
| EP | 1329160 | 7/2003 |
| EP | 1757590 A1 | 2/2007 |
| JP | 1987-153273 | 7/1987 |
| JP | 1988-174905 | 7/1988 |
| JP | 1989-226815 | 9/1989 |
| JP | 2003-212864 | 7/2003 |
| JP | 2004-051628 | 2/2004 |
| JP | 2004-292703 | 10/2004 |
| JP | 2012-188418 | 10/2012 |
| JP | 2013-075871 | 4/2013 |
| JP | 2013-082699 | 5/2013 |
| JP | 2013-082704 | 5/2013 |
| JP | 2013-107867 | 6/2013 |
| JP | 2013-129651 | 7/2013 |
| JP | 2013-129653 | 7/2013 |
| WO | 1994/013644 | 6/1994 |
| WO | 1997/036897 | 10/1997 |
| WO | 1998/049166 | 11/1998 |
| WO | 2000/035919 | 6/2000 |
| WO | 2001/12189 | 2/2001 |
| WO | 2001/034127 | 5/2001 |
| WO | 2001/090078 | 11/2001 |
| WO | 2002/083111 | 10/2002 |
| WO | 2003/008405 | 1/2003 |
| WO | 2003/072102 | 9/2003 |
| WO | 2004/041813 | 5/2004 |
| WO | 2005/070925 | 8/2005 |
| WO | 2005/074875 | 8/2005 |
| WO | 2006/023462 | 3/2006 |
| WO | 2006/033005 | 3/2006 |

(56) References Cited

FOREIGN PATENT DOCUMENTS

| | | |
|---|---|---|
| WO | 2006/046593 | 5/2006 |
| WO | 2006/103045 | 10/2006 |
| WO | 2007/005838 | 1/2007 |
| WO | 2008/090382 | 7/2007 |
| WO | 2007/087427 | 8/2007 |
| WO | 2007/098826 | 9/2007 |
| WO | 2008/005457 | 1/2008 |
| WO | 2008//079277 | 7/2008 |
| WO | 2009/149858 | 12/2009 |
| WO | 2010/006713 | 1/2010 |
| WO | 2010/009290 | 1/2010 |
| WO | 2010/012442 | 2/2010 |
| WO | 2010/033360 | 3/2010 |
| WO | 2010/048207 | 4/2010 |
| WO | 2010/060379 | 6/2010 |
| WO | 2010/075376 | 7/2010 |
| WO | 2010/129497 | 11/2010 |
| WO | 2010/133336 | 11/2010 |
| WO | 2010/146236 | 12/2010 |
| WO | 2011/003065 | 1/2011 |
| WO | 2011/043371 | 4/2011 |
| WO | 2011/045224 | 4/2011 |
| WO | 2011/045240 | 4/2011 |
| WO | 2011/048082 | 4/2011 |
| WO | 2011/091153 | 7/2011 |
| WO | 2011/101229 | 8/2011 |
| WO | 2011/126903 | 10/2011 |
| WO | 2011/128304 | 10/2011 |
| WO | 2011/134964 | 11/2011 |
| WO | 2011/138285 | 11/2011 |
| WO | 2011/163518 | 12/2011 |
| WO | 2012/000896 | 1/2012 |
| WO | 2012/004217 | 1/2012 |
| WO | 2012/007500 | 1/2012 |
| WO | 2012/035011 | 3/2012 |
| WO | 2012/052412 | 4/2012 |
| WO | 2012/061290 | 5/2012 |
| WO | 2012/070114 | 5/2012 |
| WO | 2012/102387 | 8/2012 |
| WO | 2012/108511 | 8/2012 |
| WO | 2012/147107 | 11/2012 |
| WO | 2012/168361 | 12/2012 |
| WO | 2013/000931 | 1/2013 |
| WO | 2013/010946 | 1/2013 |
| WO | 2013/010947 | 1/2013 |
| WO | 2013/062980 | 5/2013 |
| WO | 2013/062981 | 5/2013 |
| WO | 2013/064324 | 5/2013 |
| WO | 2013/156431 | 10/2013 |
| WO | 2013/156433 | 10/2013 |
| WO | 2013/162716 | 10/2013 |
| WO | 2015/058020 | 4/2015 |
| WO | 2015/058022 | 4/2015 |
| WO | 2015/058023 | 4/2015 |
| WO | 2015/058024 | 4/2015 |
| WO | 2015/058026 | 4/2015 |
| WO | 2015/058028 | 4/2015 |

OTHER PUBLICATIONS

International Search Report and Written Opinion for PCT/US2014/061005 dated Dec. 16, 2014.
International Search Report and Written Opinion for PCT/US2014/061006 dated Dec. 8, 2014.
International Search Report and Written Opinion for PCT/US2014/061007 dated Dec. 31, 2014.
International Search Report and Written Opinion for PCT/US2014/061009 dated Dec. 8, 2014.
International Search Report and Written Opinion for PCT/US2014/061010 dated Dec. 15, 2014.
International Search Report and Written Opinion for PCT/US2014/061012 dated Dec. 15, 2014.
International Search Report and Written Opinion for PCT/US2014/061014 dated Dec. 15, 2014.
International Search Report and Written Opinion for PCT/US2014/061016 dated Dec. 15, 2014.
International Search Report and Written Opinion for PCT/US2014/061022 dated Dec. 29, 2014.
International Search Report and Written Opinion for PCT/US2014/061023 dated Dec. 15, 2014.
International Search Report and Written Opinion for PCT/US2014/061024 dated Dec. 15, 2014.
International Search Report and Written Opinion for PCT/US2014/061027 dated Dec. 15, 2014.
International Search Report and Written Opinion for PCT/US2014/061029 dated Dec. 15, 2014.
International Search Report and Written Opinion for PCT/US2014/061030 dated Dec. 15, 2014.
International Search Report and Written Opinion for PCT/US2013/029615 dated May 8, 2013.
Ameduri, B. et al., "Synthesis and polymerization of fluorinated monomers bearing a reactive lateral group Part 4. Preparation of functional perfluorovinyl monomers by radical addition of functional mercaptans to 1,1,2-trifluoro-1,4-pentadiene." J. Fluorine Chemistry, 92, 77-84 (1998).
International Preliminary Report on Patentability for PCT/US2011/058578 dated Dec. 21, 2012.
International Search Report and Written Opinion for PCT/US2011/058578 dated Apr. 5, 2012.
Kadam, S.S. et al., "Synthesis and Tautomerism of Substituted Pyrazolo[4,3-c]pyrazoles." Eur. J. Chem., 6811-6822 (2013).
Gorelik; Zhumai Organicheskol khimi, 1980 (16), 1322, Abstract, Chemical Abstracts, Accession No. 1980;620652.
National Center for Biotechnology Information, PubChem Compound Database; CID=17132489,https://pubchem.ncbi.nlm.nih.gov/compound/17132489, create date Nov. 13, 2007.
Frigola; European Journal of Medicinal Chemistry 1989, 435-445.
Binz et al. "Derivatives of pyridine, etc.," CA 25:30083 (1931).
Lahm, G. et al., "Rynaxypyr: A new insecticidal anthranilic diamide that acts as a potent and selective ryanodine receptor activator," Bioorganic and Medical Chemistry Letters, 2007, 17, 6274-6279.
Giornal, F. et al., "A New Synthesis and Process Development of Bis(fluoroalkyl)pyrazoles As Novel Agrophores," Organic Process Research and Development, 2014, 18, 1002-1009.
Lieser, T. et al., "Artificial organic high polymers, VII, New acrylyl derivatives and their polymerization products," Chemische Berichte, VCH, DE, 1951, 84, 4-12.
Tanaka, N. et al., "Synthesis of pyrazole carboxylic acid via cobalt-catalyzed phase oxidation," Chemistry Letters, Chemical Society of Japan, 1991, 4, 585-588.
Ross, John R. et al. "Synthesis of 7-Substituted 5,6-Dimethyl-2,4-dioxo-1,2,4,7-tetrahydropyrrolo[2,3-d][1,3]oxazines", Synthesis, v. 1985, No. 8, Jan. 1, 1985, pp. 796-798.

* cited by examiner

PROCESSES FOR THE PREPARATION OF PESTICIDAL COMPOUNDS

CROSS-REFERENCE TO RELATED APPLICATIONS

This application claims priority under 35 U.S.C. § 119(e) to U.S. Provisional Application Ser. No. 62/440,232 filed Dec. 29, 2016, which is incorporated herein by this reference in its entirety.

TECHNICAL FIELD OF THE DISCLOSURE

This application relates to efficient and economical synthetic chemical processes for the preparation of pesticidal thioethers and pesticidal sulfoxides. Further, the present application relates to certain novel compounds necessary for their synthesis. It would be advantageous to produce pesticidal thioethers and pesticidal sulfoxides efficiently and in high yield from commercially available starting materials.

BACKGROUND

There are more than ten thousand species of pests that cause losses in agriculture. The world-wide agricultural losses amount to billions of U.S. dollars each year. Stored food pests eat and adulterate stored food. The world-wide stored food losses amount to billions of U.S. dollars each year, but more importantly, deprive people of needed food. Certain pests have developed resistance to pesticides in current use. Hundreds of pest species are resistant to one or more pesticides. The development of resistance to some of the older pesticides, such as DDT, the carbamates, and the organophosphates, is well known. But resistance has even developed to some of the newer pesticides. As a result, there is an acute need for new pesticides that has led to the development of new pesticides. Specifically, US 20130288893(A1) describes, inter alia, certain pesticidal thioethers and their use as pesticides. Such compounds are finding use in agriculture for the control of pests.

In U.S. Pat. No. 9,102,655, processes for preparing such pesticidal thioethers were described. In one embodiment, the intermediate 1c, described therein, was prepared by contacting a compound of the formula 1b, described therein, with 3-bromopyridine or 3-iodopyridine in the presence of a copper salt, an inorganic base and N,N'-dimethylethane-1,2-diamine (DMEDA) as shown in the exemplary Scheme 1 below.

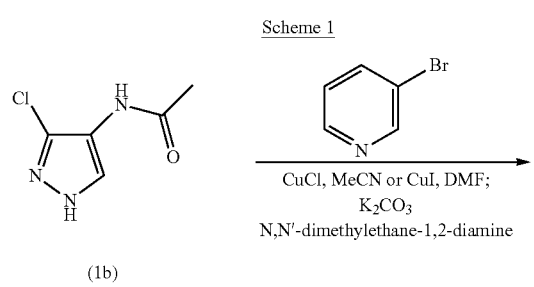

Scheme 1

CuCl, MeCN or CuI, DMF;
K₂CO₃
N,N'-dimethylethane-1,2-diamine (1b)

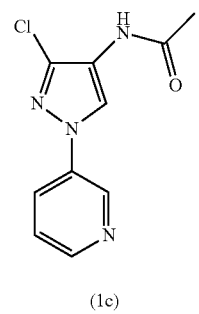

(1c)

The process, known as an Ullmann coupling, is carried out in the presence of DMEDA to serve as a ligand for the copper salt. Because DMEDA is a costly material (roughly $256/kg) and is used in amounts between about 0.4 and 0.6 molar equivalents compared to compound 1b, manufacture of the target pesticidal thioethers described in U.S. Pat. No. 9,102,655 and US Patent Publication 20130288893(A1) is more expensive.

Because there is a need for very large quantities of pesticides, particularly pesticidal thioethers of the type described in U.S. Pat. No. 9,102,655 and US Patent Publication 20130288893(A1), it would be highly advantageous to develop new processes to produce pesticidal thioethers efficiently and in high yield from economical commercially available starting materials.

Definitions of the Disclosure

The following definitions apply to the terms as used throughout this specification, unless otherwise limited in specific instances.

As used herein, the term "alkyl" includes a chain of carbon atoms, which is optionally branched including but not limited to $C_1$-$C_6$, $C_1$-$C_4$, and $C_1$-$C_3$. Illustrative alkyl groups include, but are not limited to, methyl, ethyl, n-propyl, isopropyl, n-butyl, isobutyl, sec-butyl, tert-butyl, pentyl, 2-pentyl, 3-pentyl, and the like. Alkyl may be substituted or unsubstituted. It will be understood that "alkyl" may be combined with other groups, such as those provided above, to form a functionalized alkyl. By way of example, the combination of an "alkyl" group, as described herein, with a "cycloalkyl" group may be referred to as an "alkylcycloalkyl" group.

As used herein, "halo" or "halogen" or "halide" may be used interchangeably and refers to fluorine (F), chlorine (Cl), bromine (Br) or iodine (I).

As used herein, "trihalomethyl" refers to a methyl group having three halo substituents, such as a trifluoromethyl group.

DETAILED DESCRIPTION OF THE DISCLOSURE

The compounds and process of the present disclosure are described in detail below. The processes of the present disclosure can be described according to Scheme 2.

Scheme 2

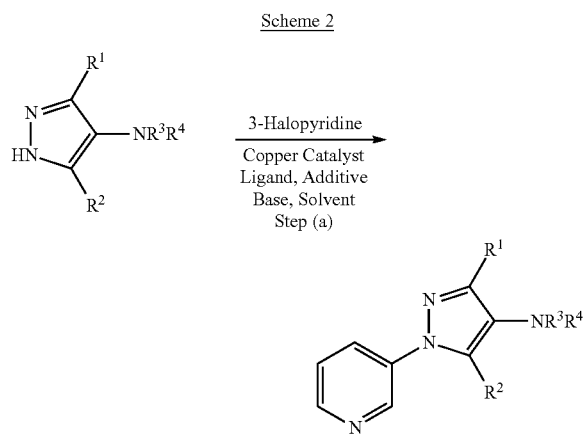

In Step (a) of Scheme 2, the pyrazole starting material, wherein each of $R^1$ and $R^2$ is independently selected from the group consisting of H, F, Cl, Br, I, $C_1$-$C_6$ alkyl and trifluoromethyl, $R^3$ is H or $C_1$-$C_6$ alkyl, and $R^4$ is H or —C(O)$C_1$-$C_6$ alkyl; can be reacted with a 3-halopyridine in the presence of a copper catalyst, a ligand, a base, a solvent and optionally an additive. In some embodiments, the 3-halopyridine can be 3-bromopyridine or 3-iodopyridine. The copper catalyst can be a copper (I) reagent or a copper (II) reagent. Exemplary copper catalysts include, but are not limited to, copper(I) chloride (CuCl), copper(II) chloride (CuCl$_2$), and copper(I) iodide (CuI). In some embodiments, the copper reagent is copper(I) chloride (CuCl). In some embodiments, the reaction can be carried out in the presence of about 0.01 to about 0.4 molar equivalents of copper catalyst compared to the pyrazole starting material. In some embodiments, the reaction can be carried out in the presence of about 0.1 to about 0.25 molar equivalents of copper catalyst compared to the pyrazole starting material. In some embodiments, the reaction can be carried out in the presence of about 0.2 molar equivalents of copper catalyst compared to the pyrazole starting material.

The base in Step (a) can be an inorganic base. Exemplary suitable bases for use in connection with Step (a) include but are not limited sodium bicarbonate (NaHCO$_3$), sodium carbonate (Na$_2$CO$_3$), calcium carbonate (CaCO$_3$), cesium carbonate (Cs$_2$CO$_3$), lithium carbonate (Li$_2$CO$_3$), potassium carbonate (K$_2$CO$_3$), lithium hydroxide (LiOH), sodium hydroxide (NaOH), potassium hydroxide (KOH), cesium hydroxide (CsOH), calcium hydroxide (Ca(OH)$_2$), sodium diphosphate (Na$_2$HPO$_4$), potassium phosphate (K$_3$PO$_4$), sodium phosphate (Na$_3$PO$_4$), sodium methoxide (NaOCH$_3$), sodium ethoxide (NaOCH$_2$CH$_3$), and the like. In some embodiments, the base is K$_3$PO$_4$ or K$_2$CO$_3$. In some embodiments, it can be advantageous to use the base in excess compared to the pyrazole starting material. In some embodiments, the base is used in about a 2-fold to about a 5-fold excess. In some embodiments, the base is used in about a 2-fold to about a 3-fold excess. In some embodiments, the base is used in about a 2-fold to excess.

The ligand in the process of Step (a) can be an amine or heteroaryl amine, such as N,N'-dimethylethane-1,2-diamine, triethylenetetramine (TETA), N,N'-bis(2-hydroxyethyl)ethylenediamine (BHEEA) and 8-hydroxyquinoline. The use of such ligands in processes for preparing pesticidal thioethers by the methods described herein contribute to the solution to the problem of efficient and economical production of such compounds on a large scale because the ligands described herein are more economical materials, such as TETA at about $4.8/kg, BHEEA at about $10-20/kg, and 8-hydroxyquinoline at about $12/kg. In some embodiments, the reaction can be carried out in the presence of less than an equimolar amount of the ligand to provide further reduction in costs. In some embodiments, the reaction can be carried out in the presence of about 0.08 to about 1.0 molar equivalents of ligand compared to the pyrazole starting material. In some embodiments, the reaction can be carried out in the presence of about 0.4 to about 0.6 molar equivalents of the ligand compared to the pyrazole starting material. In some embodiments, the reaction can be carried out in the presence of about 0.1 to about 0.2 molar equivalents of the ligand compared to the pyrazole starting material.

It was surprisingly discovered that in some embodiments of Step (a), the reaction can be carried out in the presence of an additive, such as a dialkylamine, a trialkylamine, an aryl nitrile, tetramethyleethylenediarine (TMEDA), and the like. In the presence of the additive, it was discovered that the reaction can be carried out in the presence of a reduced loading of the ligand. In some embodiments, the additive is di-n-propylamine, di-n-butylamine, benzonitrile, di-isopropylethylamine, or tetramethylethylenediamine (TMEDA). In some embodiments, the reaction of Step (a) can be carried out in the presence of about 0.5 to about 1.5 molar equivalents of the additive. In some embodiments, the reaction of Step (a) can be carried out in the presence of about 0.6 to about 1.0 molar equivalents of the additive.

Surprisingly, it has been discovered that when the ligand in Step (a) is DMEDA, and an additive is used, wherein the additive is a dialkylamine, a trialkylamine, a benzonitrile or N,N,N'N'-tetramethylethylenedinamine (TMEDA), preferably di-n-propylamine, di-n-butylamine, benzonitrile, di-isopropylethylamine, or tetramethylethylenediamine (TMEDA), that the loading of the expensive DMEDA can be lowered significantly. As noted above, typical prior art procedures for the Ullmann coupling of the type described in Step (a) involve the use of DMEDA in amounts between about 0.4 and 0.6 molar equivalents compared to the pyrazole starting material. In embodiments of the present disclosure, the reaction of Step (a) can be carried out in the presence of an additive and from about 0.05 to about 0.2 molar equivalents of DMEDA compared to the pyrazole starting material. In some embodiments, the DMEDA can be used in an amount of about 0.1 molar equivalents. It has been surprisingly discovered that under conditions where DMEDA is used in the presence of an additive, the yield of the desired product of the Ullmann coupling is higher than without the additive. Accordingly, when the reaction of Step (a) is carried out in the presence of a lower loading of DMEDA plus an additive as described herein, the process is more economical and more efficient than the processes of the prior art, such as those described in U.S. Pat. No. 9,102,655, for this substrate.

The process of Step (a) can be conducted in a solvent, such as, acetonitrile (CH$_3$CN), benzonitrile, dioxane, N,N-dimethylformamide (DMF), N-methyl-2-pyrrolidone (NMP), tetrahydrofuran (THF), toluene, 2-mthyl tetrahydrofuran, methanol (MeOH), ethanol (EtOH), and the like. In some embodiments, the solvent is N,N-dimethylformamide (DMF) or N-methyl-2-pyrrolidone (NMP). In some embodiments, it can be advantageous to carry out the reaction of Step (a) at an elevated temperature. In some embodiments, the reaction is carried out at a temperature between about 50° C. and about 150° C. In some embodiments, the reaction is carried out at a temperature between about 60° C. and about 120° C. In some embodiments, the reaction is carried out at a temperature between about 95° C. and about 115° C.

Alternatively, the processes of the present disclosure can be described according to Scheme 3.

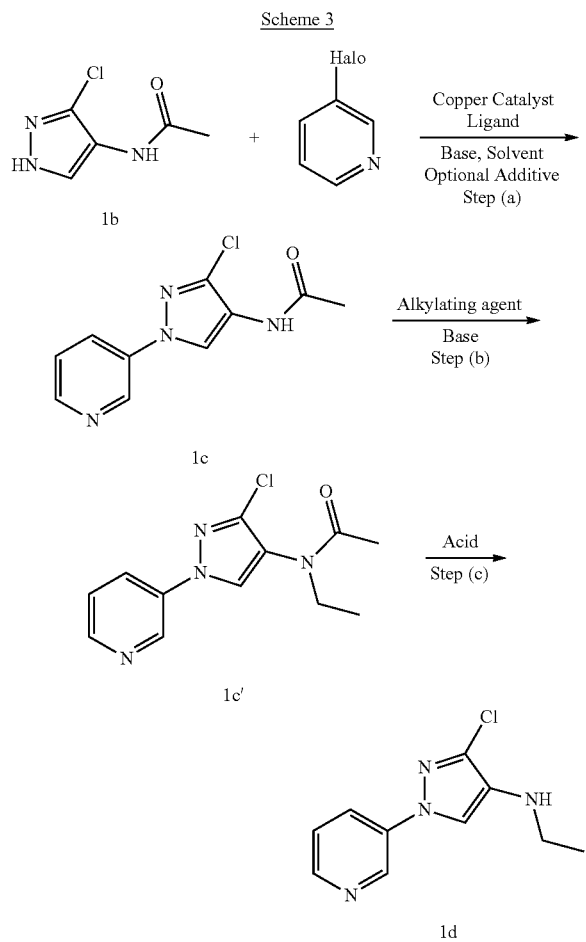

Scheme 3

In Step (a) of Scheme 3, the pyrazole starting material, 1b can be reacted with a 3-halopyridine in the presence of a copper catalyst, a ligand, a base, a solvent and optionally an additive to provide compound 1c. The copper catalyst can be a copper (I) reagent or a copper (II) reagent. Exemplary copper catalysts include, but are not limited to, copper(I) chloride (CuCl), copper(II) chloride (CuCl$_2$), and copper(I) iodide (CuI). In some embodiments, the copper reagent is copper(I) chloride (CuCl). In some embodiments, the reaction can be carried out in the presence of about 0.04 to about 0.4 molar equivalents of copper catalyst compared to the pyrazole starting material. In some embodiments, the reaction can be carried out in the presence of about 0.1 to about 0.25 molar equivalents of copper catalyst compared to the pyrazole starting material. In some embodiments, the reaction can be carried out in the presence of about 0.2 molar equivalents of copper catalyst compared to the pyrazole starting material.

The base in Step (a) can be an inorganic base. Exemplary suitable bases for use in connection with Step (a) include but are not limited sodium bicarbonate (NaHCO$_3$), sodium carbonate (Na$_2$CO$_3$), calcium carbonate (CaCO$_3$), cesium carbonate (Cs$_2$CO$_3$), lithium carbonate (Li$_2$CO$_3$), potassium carbonate (K$_2$CO$_3$), lithium hydroxide (LiOH), sodium hydroxide (NaOH), potassium hydroxide (KOH), cesium hydroxide (CsOH), calcium hydroxide (Ca(OH)$_2$), sodium diphosphate (Na$_2$HPO$_4$), potassium phosphate (K$_3$PO$_4$), sodium phosphate (Na$_3$PO$_4$), sodium methoxide (NaOCH$_3$), sodium ethoxide (NaOCH$_2$CH$_3$), and the like. In some embodiments, the base is K$_3$PO$_4$ or K$_2$CO$_3$. In some embodiments, it can be advantageous to use the base in excess compared to the pyrazole starting material. In some embodiments, the base is used in about a 2-fold to about a 5-fold excess. In some embodiments, the base is used in about a 2-fold to about a 3-fold excess. In some embodiments, the base is used in about a 2-fold to excess.

The ligand in the process of Step (a) can be an amine or heteroaryl amine, such as N,N'-dimethylethane-1,2-diamine, triethylenetetramine (TETA), N,N'-bis(2-hydroxyethyl)ethylenediamine (BHEEA) and 8-hydroxyquinoline. In some embodiments, the reaction can be carried out in the presence of about 0.08 to about 1.0 molar equivalents of ligand compared to the pyrazole starting material. In some embodiments, the reaction can be carried out in the presence of about 0.4 to about 0.6 molar equivalents of the ligand compared to the pyrazole starting material. In some embodiments, the reaction can be carried out in the presence of about 0.1 to about 0.2 molar equivalents of the ligand compared to the pyrazole starting material.

In some embodiments of Step (a), the reaction can be carried out in the presence of an additive, such as a dialkylamine, a trialkylamine, an aryl nitrile, tetramethylethylenediamine (TMEDA), and the like. In the presence of the additive, it was discovered that the reaction can be carried out in the presence of a reduced loading of the ligand. In some embodiments, the additive is di-n-propylamine, di-n-butylamine, benzonitrile, di-isopropylethylamine, or tetramethylethylenediamine (TMEDA). In some embodiments, the reaction of Step (a) can be carried out in the presence of about 0.5 to about 1.5 molar equivalents of the additive. In some embodiments, the reaction of Step (a) can be carried out in the presence of about 0.6 to about 1.0 molar equivalents of the additive.

In some embodiments, the ligand in Step (a) is DMEDA, and an additive is used, wherein the additive is a dialkylamine, a trialkylamine, a benzonitrile or N,N,N'N'-tetramethylethylenedinamine (TMEDA), preferably di-n-propylamine, di-n-butylamine, benzonitrile, di-isopropylethylamine, or tetramethylethylenediamine (TMEDA). In some embodiments, Step (a) can be carried out in the presence of an additive and between about 0.4 and 0.6 molar equivalents of DMEDA compared to the pyrazole starting material. In embodiments of the present disclosure, the reaction of Step (a) can be carried out in the presence of an additive and from about 0.05 to about 0.2 molar equivalents of DMEDA compared to the pyrazole starting material. In some embodiments, the DMEDA can be used in an amount of about 0.1 molar equivalents.

The process of Step (a) can be conducted in a solvent, such as, acetonitrile (CH$_3$CN), benzonitrile, dioxane, N,N-dimethylformamide (DMF), N-methyl-2-pyrrolidone (NMP), tetrahydrofuran (THF), 2-methyl tetrahydrofuran, toluene, methanol (MeOH), ethanol (EtOH), and the like. In some embodiments, the solvent is N,N-dimethylformamide (DMF) or N-methyl-2-pyrrolidone (NMP). In some embodiments, it can be advantageous to carry out the reaction of Step (a) at an elevated temperature. In some embodiments, the reaction is carried out at a temperature between about 50° C. and about 150° C. In some embodiments, the reaction is carried out at a temperature between about 60° C. and about 120° C. In some embodiments, the reaction is carried out at a temperature between about 95° C. and about 115° C.

In Step (b) of Scheme 3, the alkylating agent is ethane group substituted with a leaving group such as Br, I, a triflate (-OTf), a tosylate (-OTs), a mesylate (-OMs), and the like to provide a compound of the formula 1c'. In some embodiments, the alkylating agent in Step (b) is ethyl iodide or ethyl bromide. The base in Step (b) can be sodium bicarbonate (NaHCO$_3$), sodium carbonate (Na$_2$CO$_3$), calcium carbonate (CaCO$_3$), cesium carbonate (Cs$_2$CO$_3$), lithium carbonate (Li$_2$CO$_3$), potassium carbonate (K$_2$CO$_3$), lithium hydroxide (LiOH), sodium hydroxide (NaOH), potassium hydroxide (KOH), cesium hydroxide (CsOH), calcium hydroxide (Ca(OH)$_2$), sodium hydride (NaH), lithium hydride (LiH), potassium hydride (KH), sodium methoxide (NaOCH$_3$), sodium ethoxide (NaOCH$_2$CH$_3$), sodium t-butoxide (NaOt—Bu), and the like. In some embodiments, the base in Step (b) is sodium t-butoxide (NaOt—Bu).

The process in Step (b) of Scheme 3 can be carried out in the presence of a solvent. Suitable solvents include diethyl ether, methylene dichloride (DCM), N,N-dimethylformamide (DMF), tetrahydrofuran (THF), ethyl acetate (EtOAc), acetone, acetonitrile (CH$_3$CN), dioxane, dimethylsulfoxide (DMSO), nitromethane, propylene carbonate, and the like. In some embodiments, the solvent can be THF or DMF.

In Step (c) of Scheme 3, the hydrolysis can be carried out by adding an inorganic acid to the reaction mixture. The inorganic acid can be any mineral acid known in the art. In some embodiment, the mineral acid is an aqueous mineral acid. Suitable mineral acids include HF, HCl, HBr, H$_2$SO$_4$, H$_3$PO$_4$, H$_3$BO$_4$, HNO$_3$, HClO$_4$, and the like. The process of Step (c) can be conducted in a solvent, such acetonitrile (CH$_3$CN), dioxane, N-methyl-2-pyrrolidone (NMP), tetrahydrofuran (THF), toluene, methanol (MeOH), ethanol (EtOH), diethyl ether, methylene dichloride (DCM), acetone, dimethylsulfoxide (DMSO), nitromethane, propylene carbonate, and the like. In some embodiments, it can be advantageous to add water to the reaction mixture before the addition of the mineral acid.

In some embodiments, it can be advantageous to carry out the reaction of Step (c) at an elevated temperature. In some embodiments, the reaction is carried out at a temperature between about 50° C. and about 150° C. In some embodiments, the reaction is carried out at a temperature between about 60° C. and about 120° C. In some embodiments, the reaction is carried out at a temperature between about 75° C. and about 85° C. It can be advantageous to neutralize the reaction mixture following the hydrolysis with a base, such as sodium hydroxide (NaOH).

In some embodiments, the present disclosure provides processes for the preparation of pesticidal thioethers.

In some embodiments, the present disclosure provides a process for preparing a compound of the formula 1

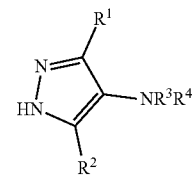

wherein each of R$^1$ and R$^2$ is independently selected from the group consisting of H, F, Cl, Br, I, C$_1$-C$_6$ alkyl and trifluoromethyl, R$^3$ is H or C$_1$-C$_6$ alkyl, and R$^4$ is H or —C(O)C$_1$-C$_6$ alkyl; comprising a. contacting a compound of the formula

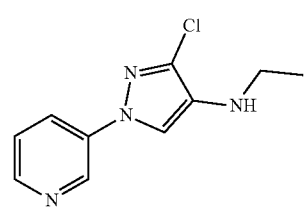

wherein each of R$^1$ and R$^2$ is independently selected from the group consisting of H, F, Cl, Br, I, C$_1$-C$_6$ alkyl and trifluoromethyl, R$^3$ is H or C$_1$-C$_6$ alkyl, and R$^4$ is H or —C(O)C$_1$-C$_6$ alkyl; with a 3-halopyridine in the presence of a copper catalyst, a ligand, a base, a solvent, and optionally an additive.

In some embodiments, the present disclosure provides a process for preparing a compound of the formula

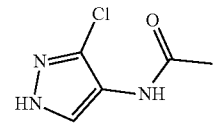

comprising a. contacting a compound of the formula 1a

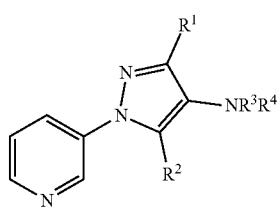

with a 3-halopyridine in the presence of a copper catalyst, a ligand, a base and optionally an additive to provide a compound of the formula 1c

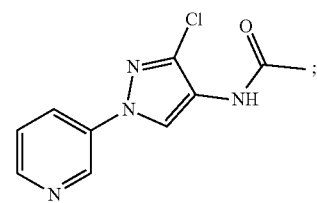 [SMILES: CC(=O)Nc1cn(-c2cccnc2)nc1Cl]

b. contacting a compound of the formula 1c

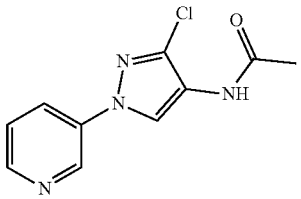 [SMILES: CC(=O)Nc1cn(-c2cccnc2)nc1Cl]

with an alkylating agent in the presence of a base to provide a compound of the formula 1c'

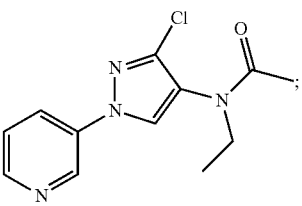 [SMILES: CCN(C(C)=O)c1cn(-c2cccnc2)nc1Cl]

c. contacting a compound of the formula 1c'

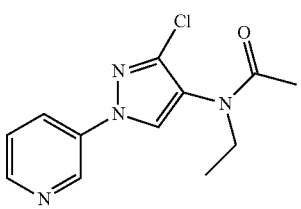 [SMILES: CCN(C(C)=O)c1cn(-c2cccnc2)nc1Cl]

with an inorganic acid to provide the compound of the formula 1d.

In some embodiments, the reactions of Step (a) and Step (b) are carried out in a single reactor. In some embodiments, the reactions of Step (a) and Step (b) are carried out in a single reactor without purification of the product of Step (a). In some embodiments, the process comprises step (a), step (b) and step (c). In some embodiments, the process comprises step (a). In some embodiments, the process comprises step (b). In some embodiments, the process comprises step (c). In some embodiments, the processes of the present disclosure can be carried out in connection with processes for preparing pesticidal thioethers, such as those described in U.S. Pat. No. 9,102,655 and US Patent Publication 20130288893(A1).

Exemplary methods for the preparation of pesticidal thioethers from compound 1d can be found in, for example, U.S. Pat. No. 9,102,654, incorporated by reference for all it discloses for preparing pesticidal thioethers from a compound of the formula 1d. Exemplary embodiments of such processes can be described as shown in Scheme 4.

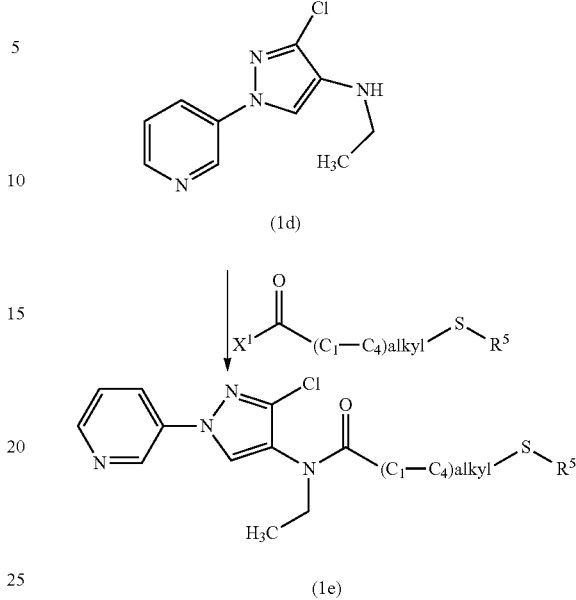

In Scheme 4, 3-chloro-N-ethyl-1-(pyridin-3-yl)-1H-pyrazol-amine (1d) is acylated with activated carbonyl thioethers, indicated as $X^1C(=O)(C_1-C_4)$-alkyl-S—$R^5$, to produce pesticidal thioethers (1e). In some embodiments, $R^5$ is $(C_1-C_4)$-haloalkyl. In some embodiments, $R^5$ is $CH_2CH_2CF_3$.

When $X^1$ is Cl, the reaction is conducted in a polar aprotic solvent such as ethyl acetate. The reaction may be optionally conducted in the presence of a base such as sodium bicarbonate, to yield pesticidal thioethers (1e).

When $X^1$ is $OC(=O)(C_1-C_4)$-alkyl, the reaction is conducted in the presence of a base preferably sodium bicarbonate, to yield pesticidal thioethers (1e). Alternatively, the reaction may be conducted when $X^1$ is an activated carboxylic acid, activated by such reagents as 2,4,6-tripropyl-trioxatriphosphinane-2,4,-trioxide ($T_3P$), carbonyldiimidazole (CDI), dicyclohexylcarbodiimide (DCC) or 1-ethyl-3-(3-dimethyl-aminopropyl)carbodiimide (EDC), preferably 2,4,6-tripropyl-trioxatriphosphinane-2,4,-trioxide and carbonyldiimidazole at temperatures of about 0° C. to about 80° C.; this reaction may also be conducted with uronium or phosphonium activating groups such as O-(7-azabenzotriazol-1-yl)-N,N,N',N'-tetramethyluronium hexafluorophosphate (HATU) or benzotriazol-1-yl-oxytripyrrolidino-phosphonium hexafluorophosphate (PyBOP), in the presence of an amine base such as diisopropylethylamine or triethylamine, in an polar aprotic solvent such as N,N-dimethylformamide, tetrahydrofuran, or dichloromethane, at temperatures of about −10° C. to about 30° C., to form pesticidal thioethers (1e).

Activated carbonyl thioethers are prepared from $X^1C(=O)(C_1-C_4)$-alkyl-S—$R^5$ wherein $X^1$ is OH, which are prepared by saponifying the corresponding ester thioethers, indicated as $X^1C(=O)(C_1-C_4)$-alkyl-S—$R^5$, wherein $X^1$ is $O(C_1-C_4)$-alkyl, with a metal hydroxide such as lithium hydroxide, in a polar solvent such as methanol or tetrahydrofuran. Alternatively, $X^1C(=O)(C_1-C_4)$-alkyl-S—$R^5$, wherein $X^1$ is OH or $O(C_1-C_4)$-alkyl may be prepared by the photochemical free-radical coupling of 3-mercaptopropionic acid and esters thereof with 3,3,3-trifluoropropene in the presence of 2,2-dimethoxy-2-phenylacetophenone initiator and long wavelength UV light in an organic solvent. Additionally, $X^1C(=O)(C_1-C_4)$-alkyl-S—$R^5$, wherein $X^1$ is OH or $O(C_1-C_4)$-alkyl may also be prepared by the low temperature free-radical initiated coupling of 3-mercaptopropionic acid and esters thereof with 3,3,3-trifluoropropene in the presence of 2,2'-azobis(4-methoxy-2,4-dimethyl) valeronitrile (V-70) initiator at temperatures of about −50° C. to about 40° C. in an organic solvent. Preferably, $X^1C(=O)(C_1-C_4)$-alkyl-S—$R^5$, wherein $X^1$ is OH or $O(C_1-C_4)$-alkyl, is prepared by the low temperature free-radical initiated coupling of 3-mercaptopropionic acid and esters thereof with 3,3,3-trifluoropropene in the presence of a two component initiator system of benzoyl peroxide and dimethylaniline or N-phenyldiethanolamine at temperatures of about −50° C. to about 40° C. in an polar aprotic solvent such as toluene or ethyl acetate.

EXAMPLES

These examples are for illustration purposes and are not to be construed as limiting this disclosure to only the embodiments disclosed in these examples.

Starting materials, reagents, and solvents that were obtained from commercial sources were used without further purification. Melting points are uncorrected. Examples using "room temperature" were conducted in climate controlled laboratories with temperatures ranging from about 20° C. to about 24° C. Molecules are given their known names, named according to naming programs within Accelrys Draw, ChemDraw, or ACD Name Pro. If such programs are unable to name a molecule, such molecule is named using conventional naming rules. $^1$H NMR spectral data are in ppm (δ) and were recorded at 300, 400, 500, or 600 MHz; $^{13}$C NMR spectral data are in ppm (δ) and were recorded at 75, 100, or 150 MHz, and $^{19}$F NMR spectral data are in ppm (δ) and were recorded at 376 MHz, unless otherwise stated.

N-(3-chloro-1H-pyrazol-4-yl)acetamide, compound 1b, was prepared according to the method described in U.S. Pat. No. 9,029,554, incorporated herein by reference for the preparation of compound 1b. 3-((3,3,3-trifluoropropyl)thio) propanoyl chloride was prepared according to the methods described in U.S. Pat. No. 9,102,655, incorporated herein by reference for the preparation of 3-((3,3,3-trifluoropropyl) thio)propanoyl chloride.

Compound Examples

Example 1

N-(3-Chloro-1-(pyridin-3-yl)-1H-pyrazol-4-yl)acetamide (1c)

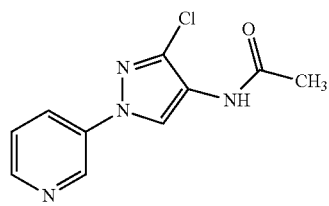 [SMILES: CC(=O)Nc1cn(-c2cccnc2)nc1Cl]

To a 25 mL three necked round-bottomed flask was added N-(3-chloro-1H-pyrazol-4-yl)acetamide (2.00 g, 12.5 mmol), potassium carbonate (3.46 g, 25.0 mmol), and 3-bromopyridine (1.45 mL, 15.0 mmol). Anhydrous N-methylpyrrolidone (10.0 mL) was added, and the mixture was sparged with nitrogen for 30 minutes. Copper(I) chloride (0.248 g, 0.250 mmol, 0.2 equivalents) and N,N'-bis(2-hydroxyethyl)ethylenediamine (0.743 g, 5.00 mmol, 0.4 equivalents) were added. The mixture was sparged with nitrogen for 10 minutes. The mixture was stirred at 95° C. for 6 hours. The light yellow green mixture was cooled down, and water (10 mL) was added over 5 minutes. The mixture was transferred into 100 mL flask with water (20 mL). The mixture was stirred for 1 hour and filtered. The filter cake was washed with cold water (2×5 mL). Acetonitrile (30 mL) was used to rinse and completely transfer the wet cake into a 100 mL flask. The mixture was concentrated to afford the title compound as an off-white solid powder (90.8 weight percent, 2.55 g, 81%): $^1$H NMR (400 MHz, DMSO-d$_6$) δ 9.94 (br.s, 1H), 9.05 (s, 1H), 8.81 (s, 1H), 8.54 (d, J=4.3 Hz, 1H), 8.20 (ddd, J=8.4, 2.8, 1.4 Hz, 1H), 7.54 (dd, J=8.4, 4.7 Hz, 1H), 2.10 (s, 3H); ESIMS m/z 237 ([M+H]$^+$).

Alternate Synthetic Route to N-(3-chloro-1-(pyridin-3-yl)-1H-pyrazol-4-yl)acetamide (1c)

To a 25 mL three necked round-bottomed flask was added N-(3-chloro-1H-pyrazol-4-yl)acetamide (2.00 g, 12.5 mmol), potassium carbonate (3.46 g, 25.0 mmol), and 3-bromopyridine (1.45 mL, 15.0 mmol). Anhydrous N-methylpyrrolidone (10.0 mL) was added, and the mixture was sparged with nitrogen for 30 minutes. Copper(I) iodide (0.238 g, 1.25 mmol, 0.1 equivalents) and N,N'-bis(2-hydroxyethyl)ethylenediamine (0.372 g, 2.50 mmol, 0.2 equivalents) were added. The mixture was sparged with nitrogen for 15 minutes. The mixture was stirred at 95° C. for 48 hours. The light yellow green mixture was cooled down, water (10 mL) was added over 5 minutes. The mixture was transferred into 100 mL flask with water (20 mL). The mixture was stirred for 1 hour, then filtered. The filter cake was washed with cold water (2×5 mL). Acetonitrile (30 mL) was used to rinse and completely transfer the wet cake. The mixture was concentrated to provide the title compound as an off-white solid powder (87.6% weight percent, 2.59 g, 79%). Characterization matched sample prepared by previous method.

Alternate Synthetic Route to N-(3-chloro-1-(pyridin-3-yl)-1H-pyrazol-4-yl)acetamide (1c)

To a 25 mL three necked round-bottomed flask was added N-(3-chloro-1H-pyrazol-4-yl)acetamide (2.00 g, 12.5 mmol), potassium carbonate (3.46 g, 25.0 mmol), and 3-bromopyridine (1.45 mL, 15.0 mmol). Anhydrous N-methylpyrrolidone (10.0 mL) was added, and the mixture was sparged with nitrogen for 30 minutes. Copper(I) chloride (0.248 g, 0.250 mmol, 0.2 equivalents), and N,N'-bis(2-aminoethyl)-1,2-ethanediamine (0.747 mL, 5.00 mmol, 0.4 equivalents) were added. The mixture was sparged with nitrogen for 10 minutes. The mixture was stirred at 95° C. for 6 hours. The light yellow green mixture was cooled down, and water (10 mL) was added over 5 minutes. The mixture was transferred into 100 mL flask with water (20 mL). The mixture was stirred for 1 hour, then filtered. The filter cake was washed with cold water (2×5 mL). The wet cake was dried to provide the title compound as an off-white solid powder (64.8 weight percent, 1.17 g, 60%). Characterization matched sample prepared by previous method.

Alternate Synthetic Route to N-(3-chloro-1-(pyridin-3-yl)-1H-pyrazol-4-yl)acetamide (1c)

To a 25 mL three necked round-bottomed flask was added N-(3-chloro-1H-pyrazol-4-yl)acetamide (2.00 g, 12.5 mmol), potassium carbonate (3.46 g, 25.0 mmol), and 3-bromopyridine (1.81 mL, 18.8 mmol). Anhydrous N-methylpyrrolidone (10.0 mL) was added, and the mixture was sparged with nitrogen for 30 minutes. Copper(I) chloride (0.124 g, 1.25 mmol, 0.1 equivalents), and N,N'-bis(2-aminoethyl)-1,2-ethanediamine (0.367 g, 2.5 mmol, 0.2 equivalents) were added. The mixture was sparged with nitrogen for 15 minutes. The mixture was stirred at 95° C. for 22 hours. The brown mixture was cooled down, and water (10 mL) was added over 5 minutes. The mixture was transferred into 100 mL flask with water (20 mL). The mixture was stirred for 1 hour, then filtered. The filter cake was washed with cold water (2×5 mL). Acetonitrile (30 mL) was used to rinse and completely transfer the wet cake into a 100 mL flask. The mixture was concentrated to provide the title compound as an off-white solid powder (79.7 weight percent, 1.99 g, 69%). Characterization matched sample prepared by previous method.

Alternate Synthetic Route to N-(3-chloro-1-(pyridin-3-yl)-1H-pyrazol-4-yl)acetamide (1c)

To a 25 mL three necked round-bottomed flask was added N-(3-chloro-1H-pyrazol-4-yl)acetamide (2.00 g, 12.5 mmol), potassium carbonate (3.46 g, 25.0 mmol), and anhydrous N-methylpyrrolidone (10.0 mL). 3-Bromopyridine (1.20 mL, 12.5 mmol, 1.0 equivalent) was added, and the mixture was sparged with nitrogen for 30 minutes. Copper(I) chloride (0.248 g, 2.5 mmol, 0.2 equivalents), and triethylenetetramine (TETA) (N,N'-bis(2-aminoethyl)-1,2-ethanediamine 64-69%, 0.560 mL, 2.5 mmol, 0.2 equivalents) were added. The mixture was sparged with nitrogen for 10 minutes. The mixture was stirred at 95° C. Additional 3-bromopyridine in 5 shots (0.120 mL, 0.1 equivalents per shot) was added at 2 hours, 3.5 hours, 5 hours, 6.5 hours, and 9 hours. Additional TETA in 4 shots (0.280 mL, 0.1 equivalents per shot) was added at 2 hours, 3.5 hours, 5 hours, and 6.5 hours. The reaction was stopped after 15 hours. The dark blue mixture was cooled down, and water (10 mL) was added over 5 minutes. The mixture was transferred into 100 mL flask with water (20 mL). The mixture was stirred for 1 hour, then filtered. The filter cake was washed with cold water (2×10 mL). The wet cake was dried at 50° C. in a vacuum oven providing the title compound (97.3 weight percent, 2.27 g, 79%). Characterization matched sample prepared by previous method.

Alternate Synthetic Route to N-(3-chloro-1-(pyridin-3-yl)-1H-pyrazol-4-yl)acetamide (1c)

To a 25 mL three necked round-bottomed flask was added N-(3-chloro-1H-pyrazol-4-yl)acetamide (2.00 g, 12.5 mmol), potassium carbonate (3.46 g, 25.0 mmol), and anhydrous N-methylpyrrolidone (10.0 mL). 3-Bromopyridine (1.20 mL, 10.0 mmol, 1.0 equivalent) was added, and the mixture was sparged with nitrogen for 30 minutes. Copper(I) chloride (0.248 g, 2.50 mmol, 0.2 equivalents), and Amine Multi-Use Emulsifier (N,N'-bis(2-aminoethyl)-1,2-ethanediamine 73.8%, 0.500 mL, 2.50 mmol, 0.2 equivalents) were added. The mixture was sparged with nitrogen for 15 minutes. The mixture was stirred at 95° C. Additional 3-bromopyridine in 7 shots (0.115 mL, 0.1 equivalents per shot) was added at 2 hours, 3.5 hours, 5 hours, 6.5 hours, 8 hours, 9.5 hours, and 11 hours. Additional Amine Multi-Use Emulsifier in 4 shots (0.245 mL, 0.1 equivalents per shot) was added at 2 hours, 3.5 hours, 5 hours, and 6.5 hours. The reaction was stopped at 15 hours. The dark blue mixture was cooled down, and water (10 mL) was added over 5 minutes. The mixture was transferred into 100 mL flask with water (20 mL). The mixture was stirred for 1 hour. The filter cake was washed with cold water (3×10 mL). The wet cake was dried at 50° C. in a vacuum oven to provide the title compound (97.2 weight percent, 2.36 g, 82%). Characterization matched sample prepared by previous method.

Example 2

N-(3-Chloro-1-(pyridin-3-yl)-1H-pyrazol-4-yl)-N-ethylacetamide (1c')

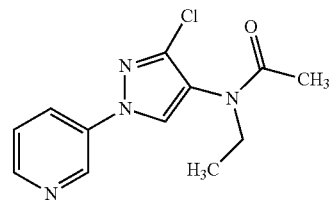 [SMILES: CCN(C(C)=O)c1cn(-c2cccnc2)nc1Cl]

A three-neck round bottomed flask (100 mL) was charged with N-(3-chloro-1-(pyridin-3-yl)-1H-pyrazol-4-yl)acetamide (5.00 g, 21.1 mmol) and tetrahydrofuran (50 mL). Sodium tert-butoxide (3.05 g, 31.7 mmol) was added (causing a temperature rise from 22° C. to 27.9° C.), followed by bromoethane (4.70 mL, 63.4 mmol). The reaction was stirred at 35° C. for 168 hours, at which point HPLC analysis indicated that only 2.9% (area under the curve, AUC) starting material remained. The reaction mixture was concentrated to give a brown residue, which was diluted with ethyl acetate (50 mL) and water (50 mL). The aqueous layer was extracted with ethyl acetate (4×50 mL) and the combined organics were concentrated to give a brown residue. The residue was dissolved in dichloromethane (2×10 mL) and purified by flash column chromatography using 60-100% ethyl acetate/hexanes as eluent. The fractions containing pure product were combined and concentrated to afford the title product as a yellow solid (4.20 g, 74%): $^1$H NMR (400 MHz, CDCl$_3$) δ 8.98 (d, J=2.7, 0.8 Hz, 1H), 8.62 (dd, J=4.8, 1.4 Hz, 1H), 8.06 (ddd, J=8.3, 2.7, 1.4 Hz, 1H), 8.00 (s, 1H), 7.47 (dd, J=8.3, 4.7 Hz, 1H), 3.71 (q, J=7.1 Hz, 2H), 1.97 (s, 3H), 1.16 (t, J=7.2 Hz, 3H); $^{13}$C NMR (101 MHz, CDCl$_3$) δ 170.69, 148.56, 140.89, 139.95, 135.64, 126.22, 126.08, 124.86, 124.09, 43.77, 22.27, 13.15; mp 87-91° C.; ESIMS m/z 265 ([M+H]$^+$).

Alternate Synthetic Route to N-(3-chloro-1-(pyridin-3-yl)-1H-pyrazol-4-yl)-N-ethylacetamide (1c')

A three-neck round bottomed flask (100 mL) was charged with N-(3-chloro-1-(pyridin-3-yl)-1H-pyrazol-4-yl)acetamide (1.66 g, 7.0 mmol) and tetrahydrofuran (16 mL). Sodium tert-butoxide (0.843 g, 8.77 mmol, 1.25 equivalent) and bromoethane (0.78 mL, 10.52 mmol, 1.5 equivalent) were added and the reactor was capped with a septa. The reaction was stirred at 58° C. for 24 hours, at which point HPLC analysis indicated that only 1.97% starting material remained. The mixture was concentrated to give a brown residue, which was dissolved in water (20 mL) and ethyl acetate (20 mL). The aqueous layer was extracted with ethyl acetate (2×20 mL) and the combined organics were concentrated to dryness. The residue was passed through a silica gel plug (40 g silica) and eluted with ethyl acetate (200 mL). The filtrates were concentrated to dryness and further dried under vacuum at 20° C. to afford a yellow solid (1.68 g, 89%). Characterization matched sample prepared by previous method.

Alternate Synthetic Route to N-(3-chloro-1-(pyridin-3-yl)-1H-pyrazol-4-yl)-N-ethylacetamide (1c')

In a three-neck round bottomed flask (125 mL) was added N-(3-chloro-1-(pyridin-3-yl)-1H-pyrazol-4-yl)acetamide (2.57 g, 9.44 mmol), tetrahydrofuran (55 mL), and sodium tert-butoxide (1.81 g, 18.9 mmol). The suspension was stirred for 5 minutes then bromoethane (1.41 mL, 18.9 mmol), and tetrabutylammonium iodide (0.0670 g, 0.200 mmol) were added. The resulting gray colored suspension was then heated to 38° C. The reaction was analyzed after 3 hours and found to have gone to 81% completion, after 24 hours the reaction was found to have gone to completion. The reaction mixture was allowed to cool to ambient temperature and quenched with ammonium hydroxide/formic acid buffer (10 mL). The mixture was then diluted with tetrahydrofuran (40 mL), ethyl acetate (120 mL), and saturated sodium bicarbonate (30 mL). The layers were separated and the aqueous layer was extracted with ethyl acetate (2×30 mL). The organic layers were combined and silica (37 g) was added. The solvent was removed in vacuo to give a solid that was purified using semi-automated silica gel chromatography (RediSep Silica 220 g column; Hexanes (0.2% triethylamine)/ethyl acetate, 40/60 to 0/100 gradient elution system, flow rate 150 mL/minute) to give, after concentration, an orange solid (2.19 g, 88%). Characterization matched sample prepared by previous method.

Example 3

3-Chloro-N-ethyl-1-(pyridin-3-yl)-1H-pyrazol-4-amine (1 d)

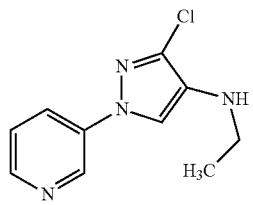

A solution of N-(3-chloro-1-(pyridin-3-yl)-1H-pyrazol-4-yl)-N-ethylacetamide (1.8 g, 6.80 mmol) in hydrochloric acid (1 N, 34 mL) was heated at 80° C. for 18 hours, at which point HPLC analysis indicated that only 1.1% starting material remained. The reaction mixture was cooled to 20° C. and basified with sodium hydroxide (50 weight percent) to pH>9. The resulting suspension was stirred at 20° C. for 2 hours and filtered. The filter cake was rinsed with water (2×5 mL), conditioned for 30 minutes, and air-dried to afford an off-white solid (1.48 g, 95%): $^1$H NMR (400 MHz, DMSO-$d_6$) δ 9.00 (dd, J=2.8, 0.8 Hz, 1H), 8.45 (dd, J=4.7, 1.4 Hz, 1H), 8.11 (ddd, J=8.4, 2.8, 1.4 Hz, 1H), 8.06 (d, J=0.6 Hz, 1H), 7.49 (ddd, J=8.4, 4.7, 0.8 Hz, 1H), 4.63 (t, J=6.0 Hz, 1H), 3.00 (qd, J=7.1, 5.8 Hz, 2H), 1.19 (t, J=7.1 Hz, 3H); $^{13}$C NMR (101 MHz, DMSO-$d_6$) δ 146.18, 138.31, 135.78, 132.82, 130.84, 124.08, 123.97, 112.23, 40.51, 14.28; ESIMS m/z 223 ([M+H]+).

Alternate Synthetic Route to 3-chloro-N-ethyl-1-(pyridin-3-yl)-1H-pyrazol-4-amine (1d)

A three-neck round bottomed flask (100 mL) was charged with N-(3-chloro-1-(pyridin-3-yl)-1H-pyrazol-4-yl)acetamide (0.475 mg, 2.01 mmol) and tetrahydrofuran (10 mL). Borontrifluoride etherate (0.630 mL, 5.02 mmol) was added and the mixture was stirred for 15 minutes to give a suspension. Sodium borohydride (0.228 g, 6.02 mmol) was added and the reaction was heated at 60° C. for 4 hours, at which point thin layer chromatography analysis [Eluent: ethyl acetate, sample was prepared by treatment of reaction mixture with hydrochloric acid, followed by sodium bicarbonate basification and ethyl acetate extraction] indicated that the reaction was complete. Water (10 mL) and concentrated hydrochloric acid (1 mL) were added and the reaction was heated at 60° C. for 1 hour. The reaction mixture was cooled to room temperature and distilled to remove tetrahydrofuran. The mixture was neutralized with saturated aqueous sodium bicarbonate to pH ~8 to afford a suspension, which was stirred for 1 hour and filtered. The filter cake was rinsed with water (10 mL) and dried under vacuum to afford a white solid (0.352 g, 79%). Characterization matched sample prepared by previous method.

Alternate Synthetic Route to 3-chloro-N-ethyl-1-(pyridin-3-yl)-1H-pyrazol-4-amine (1d)

To a 25 mL round-bottomed flask was added N-(3-chloro-1-(pyridin-3-yl)-1H-pyrazol-4-yl)acetamide (1.0 g, 4.2 mmol), and anhydrous tetrahydrofuran (6.0 mL). The white suspension was cooled in an ice-water bath to 6° C. Sodium bis(2-methoxyethoxy)aluminumhydride (Red-Al, 60 wt % in toluene, 3.5 mL, 11 mmol) was added slowly via syringe over 10 minutes while keeping the temperature below 10° C. The thick suspension gradually turned clear yellow solution during the addition. The reaction mixture was slowly warmed up to 25° C. over 1.5 hours. The solution was heated to 50° C. and stirred for 4.5 hours. The solution was cooled down to 20° C. Sodium hydroxide (2 M, 5.0 mL) was added to quench the reaction. Water (20 mL) was added giving two clear, well separated phases. The bottom aqueous phase was separated and extracted with ethyl acetate (2×20 mL). The combined organic layers were dried over anhydrous sodium sulfate, filtered, and concentrated to afford the crude product as a red-brown oil (78 weight percent, 0.59 g, 63%). Characterization matched sample prepared by previous method.

Alternate Synthetic Route to 3-chloro-N-ethyl-1-(pyridin-3-yl)-1H-pyrazol-4-amine (1d)

To a 25 mL round-bottomed flask was added N-(3-chloro-1-(pyridin-3-yl)-1H-pyrazol-4-yl)acetamide (1.0 g, 4.2 mmol), and anhydrous tetrahydrofuran (9 mL). The white suspension was cooled in an ice-water bath to 5° C. Sodium bis(2-methoxyethoxy)aluminumhydride (Red-Al, Aldrich, 60 wt % in toluene, 4.3 mL, 13 mmol) was added slowly via syringe over 15 minutes while keeping the temperature below 10° C. The thick suspension gradually turned clear yellow solution during the addition. The reaction mixture was slowly warmed up to 25° C. over 3 hours, then was stirred at 25° C. for 17 hours. Sodium hydroxide (2 M, 8 mL) was added to quench the reaction. Water (20 mL) was added, and the two layers were separated. The bottom aqueous phase was extracted with diethyl ether (3×20 mL). The combined organic layers were dried over anhydrous sodium sulfate, filtered, and concentrated to afford the crude product as a red-brown oil (61 weight percent, 0.56 g, 59%). Characterization matched sample prepared by previous method.

Alternate Synthetic Route to 3-chloro-N-ethyl-1-(pyridin-3-yl)-1H-pyrazol-4-amine (1d) in a Three Step Telescoped Process Containing Ullmann Coupling, Alkylation and Hydrolysis Step 1: Synthesis of N-(3-chloro-1-(pyridin-3-yl)-1H-pyrazol-4-yl)acetamide (1c):

To a 250 mL four necked flat bottom flask was introduced N-(3-chloro-1H-pyrazol-4-yl)acetamide (10.0 g, 60.8 mmol), $K_2CO_3$ (17.2 g, 122 mmol), anhydrous NMP (26.0 mL) and 3-Bromopyridine (7.25 mL, 74.5 mmol, 1.2 eq.). The mixture was sparged with $N_2$ for 50 min. CuCl (608 mg, 6.08 mmol, 0.1 eq.) and N,N'-dimethyl ethylenediamine (DMEDA, 1.35 mL, 12.1 mmol, 0.2 eq.) were added. The resultant light-green mixture was sparged with $N_2$ for 15 min and was stirred at 95° C. LC indicated 98% conversion at 5 h. The blue suspension was cooled down to room temperature and used directly in the next step without any isolation.

Step 2: Synthesis of N-(3-chloro-1-(pyridin-3-yl)-1H-pyrazol-4-yl)-N-ethylacetamide (1c'):

To the 250 mL four necked flat bottom flask containing N-(3-chloro-1-(pyridin-3-yl)-1H-pyrazol-4-yl)acetamide crude solution in NMP (~60.8 mmol) was added anhydrous NMP (6.0 mL). To the dark blue suspension was added sodium tert-butoxide (14.5 g, 146 mmol, 2.4 eq.) portionwise over 20 min (pot temp gradually raised from 24° C. to 37° C.). The resultant dark brown suspension was cooled down to 19° C. in an ice-water bath. Bromoethane (9.17 mL, 122 mmol, 2.0 eq.) was added dropwise via syringe over 15 min under nitrogen. The mixture turned yellow-green then became a dark brown suspension. The mixture was allowed to warm up slowly to 36° C. giving a yellow-green suspension. LC indicated 87% conversion at 3 h. Additional sodium tert-butoxide (1.21 g, 12.2 mmol, 0.2 eq.) was added and the mixture was stirred for another 2 h. LC indicated 97% conversion. The yellow suspension was then sparged with $N_2$ at 70° C. for 1.5 h and cooled down to room temperature. The crude solution was used directly in the next step without any isolation.

Step 3: Synthesis of 3-chloro-N-ethyl-1-(pyridin-3-yl)-1H-pyrazol-4-amine (1d):

The light brown mixture of crude N-(3-chloro-1-(pyridin-3-yl)-1H-pyrazol-4-yl)-N-ethylacetamide (~60.8 mmol) in NMP in the 250 mL four necked flat bottom flask was cooled down to 15° C. in an ice-water bath and stirred vigorously. Aqueous HCl (6.0 M, 86.5 mL, 8.5 eq.) was added slowly over 40 min (Caution: Gasing due to $CO_2$ release!) leading to a dark brown solution with small amount of brown solid powder. The mixture was stirred at 80° C. for 16 h and LC indicated full conversion. The solution was cooled down to 20° C. in an ice-water bath. NaOH solution (25 wt % in $H_2O$, 33 mL) was added over 50 min leading to a yellow suspension. Ammonium hydroxide (29 wt %, 5.0 mL) was added and the brown suspension was stirred for 10 min. The mixture was filtered through a glass funnel. The brown wet cake was washed with ammonium hydroxide (29 wt %, 20 mL) and water (3×45 mL) giving a yellow brown wet cake.

The wet cake was dried in vacuum oven at 50° C. for 16 h to afford product as brown solid powder (96% weight percent, 9.96 g, 73.6% over 3 steps).

$^1$H NMR (400 MHz, DMSO-$d_6$) δ 8.99 (dd, J=2.8, 0.8 Hz, 1H), 8.44 (dd, J=4.7, 1.4 Hz, 1H), 8.10 (ddd, J=8.4, 2.8, 1.4 Hz, 1H), 8.05 (d, J=0.6 Hz, 1H), 7.49 (ddd, J=8.4, 4.7, 0.8 Hz, 1H), 4.60 (t, J=6.0 Hz, 1H), 3.00 (qd, J=7.1, 5.9 Hz, 2H), 1.18 (t, J=7.1 Hz, 3H). $^{13}$C NMR (101 MHz, DMSO-$d_6$) δ 146.17, 138.33, 135.79, 132.81, 130.87, 124.05, 123.98, 112.23, 40.53, 14.28. ESIMS m/z: 223 ([M+H]$^+$)

Example 4

N-(3-Chloro-1-(pyridin-3-yl)-1H-pyrazol-4-yl)-N-ethyl-3-((3,3,3-trifluoropropyl)thio)propanamide (Compound 6.9)

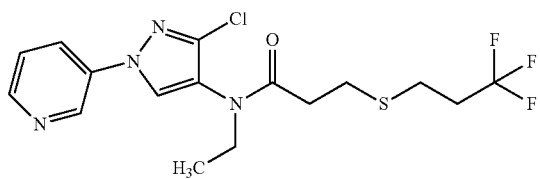 [SMILES: CCN(C(=O)CCSCCC(F)(F)F)c1cn(-c2cccnc2)nc1Cl]

A three-neck round bottomed flask (100 mL) was charged with 3-chloro-N-ethyl-1-(pyridin-3-yl)-1H-pyrazol-amine (5.00 g, 22.5 mmol) and ethyl acetate (50 mL). Sodium bicarbonate (4.72 g, 56.1 mmol) was added, followed by dropwise addition of 3-((3,3,3-trifluoropropyl)thio)propanoyl chloride (5.95 g, 26.9 mmol) at <20° C. for 2 hours, at which point HPLC analysis indicated that the reaction was complete. The reaction was diluted with water (50 mL) (off-gassing) and the layers were separated. The aqueous layer was extracted with ethyl acetate (20 mL) and the combined organic layers were concentrated to dryness to afford a light brown solid (10.1 g, quantitative). A small sample of crude product was purified by flash column chromatography using ethyl acetate as eluent to obtain an analytical reference sample: mp 79-81° C.; $^1$H NMR (400 MHz, DMSO-$d_6$) δ 9.11 (d, J=2.7 Hz, 1H), 8.97 (s, 1H), 8.60 (dd, J=4.8, 1.4 Hz, 1H), 8.24 (ddd, J=8.4, 2.8, 1.4 Hz, 1H), 7.60 (ddd, J=8.4, 4.7, 0.8 Hz, 1H), 3.62 (q, J=7.2 Hz, 2H), 2.75 (t, J=7.0 Hz, 2H), 2.66-2.57 (m, 2H), 2.57-2.44 (m, 2H), 2.41 (t, J=7.0 HZ, 2H), 1.08 (t, J=7.1 HZ, 3H); ESIMS M/Z 407 ([M+H]$^+$).

Example 5

3-Chloro-N-(3-chloro-1-(pyridin-3-yl)-1H-pyrazol-4-yl)-N-ethylpropanamide (2a)

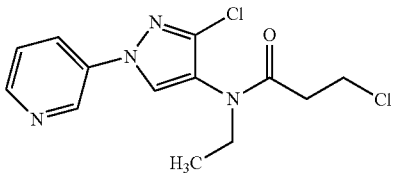 [SMILES: CCN(C(=O)CCCl)c1cn(-c2cccnc2)nc1Cl]

A three-neck round bottomed flask (100 mL) was charged with 3-chloro-N-ethyl-1-(pyridin-3-yl)-1H-pyrazol-amine (2.00 g, 8.98 mmol), ethyl acetate (20 mL), sodium bicarbonate (1.89 g, 22.5 mmol) was added, followed by dropwise addition of 3-chloropropanoyl chloride (1.37 g, 10.78 mmol) at <20° C. The reaction was stirred at 10° C. for 2 hours, at which point thin layer chromatography analysis indicated that the reaction was complete [Eluent: ethyl acetate]. The reaction was diluted with water (50 mL) (off-gassing) and the layers were separated. The aqueous layer was extracted with ethyl acetate (20 mL) and the combined organic layers were concentrated to dryness to afford a light brown oil which was purified by flash column chromatography using 80% ethyl acetate/hexanes as eluent. The pure fractions were concentrated to afford a white solid (1.8 g, 64%): mp 87-90° C.; $^1$H NMR (400 MHz, DMSO-$d_6$) δ 9.11 (dd, J=2.7, 0.7 Hz, 1H), 8.98 (s, 1H), 8.61 (dd, J=4.7, 1.4, 1 H), 8.25 (ddd, J=8.4, 2.7, 1.4 Hz, 1H), 7.61 (ddd, J=8.3, 4.7, 0.8 Hz, 1H), 3.78 (t, J=6.3 Hz, 2H), 3.63 (q, J=7.1 Hz, 2H), 2.62 (t, J=6.2 Hz, 2H), 1.10 (t, J=7.1 Hz, 3H); $^{13}$C NMR (101 MHz, DMSO-$d_6$) δ 169.13, 148.13, 139.71, 139.12, 135.27, 129.42, 125.84, 124.24, 122.38, 43.12, 40.10, 36.28, 12.78; EIMS m/z 312 ([M]$^+$).

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

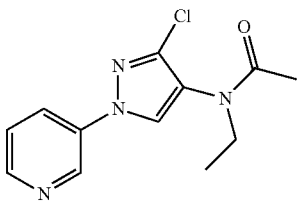

What is claimed is:

1. A process for preparing a compound of the formula 1

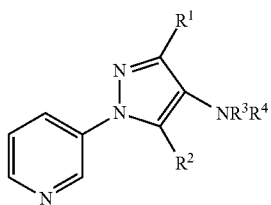

wherein each of R$^1$ and R$^2$ is independently selected from the group consisting of H, F, Cl, Br, I, C$_1$-C$_6$ alkyl and trifluoromethyl, R$^3$ is H or C$_1$-C$_6$ alkyl, and R$^4$ is H or —C(O)C$_1$-C$_6$ alkyl; comprising
 a. contacting a compound of the formula

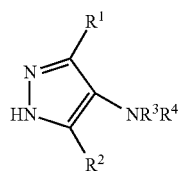

wherein each of R$^1$ and R$^2$ is independently selected from the group consisting of H, F, Cl, Br, I, C$_1$-C$_6$ alkyl and trifluoromethyl, R$^3$ is H or C$_1$-C$_6$ alkyl, and R$^4$ is H or —C(O)C$_1$-C$_6$ alkyl; with a 3-halopyridine in the presence of a copper catalyst, a ligand, a base, a solvent and an additive.

2. The process of claim 1, wherein the copper catalyst in step (a) is copper (I) chloride (CuCl), copper (II) chloride (CuCl$_2$), copper (I) bromide (CuBr) or copper (I) iodide (CuI).

3. The process of claim 1, wherein the ligand in step (a) is selected from the group consisting of triethylenetetramine (TETA), N,N'-bis(2-hydroxyethyl)ethylenediamine (BHEEA) and 8-hydroxyquinoline.

4. The process of claim 1, wherein the additive is used, and the additive is a dialkylamine, a trialkylamine, a benzonitrile or N,N,N'N'-tetramethylethylenedinamine (TMEDA).

5. The process of claim 1, wherein the ligand in step (a) is N,N'-dimethylethane-1,2-diamine (DMEDA), and the additive is used and the additive is a dialkylamine, a trialkylamine, a benzonitrile or N,N,N'N'-tetramethylethylenedinamine (TMEDA).

6. The process of claim 1, wherein the base in step (a) is selected from the group consisting of sodium bicarbonate (NaHCO$_3$), sodium carbonate (Na$_2$CO$_3$), calcium carbonate (CaCO$_3$), cesium carbonate (Cs$_2$CO$_3$), lithium carbonate (Li$_2$CO$_3$), potassium carbonate (K$_2$CO$_3$), lithium hydroxide (LiOH), sodium hydroxide (NaOH), potassium hydroxide (KOH), cesium hydroxide (CsOH), calcium hydroxide (Ca(OH)$_2$), sodium diphosphate (Na$_2$HPO$_4$), potassium phosphate (K$_3$PO$_4$), sodium phosphate (Na$_3$PO$_4$), sodium methoxide (NaOCH$_3$) and sodium ethoxide (NaOCH$_2$CH$_3$).

7. The process of claim 1, wherein the solvent of step (a) is acetonitrile (CH$_3$CN), benzonitrile, dioxane, N,N-dimethylformamide (DMF), N-methyl-2-pyrrolidone (NMP), tetrahydrofuran (THF), dimethylsulfoxide (DMSO), 2-methyl tetrahydrofuran, toluene, methanol (MeOH), or ethanol (EtOH).

8. The process of claim 1, wherein the 3-halopyridine is 3-bromopyridine.

9. The process of claim 1, wherein R$^3$ is H.

10. The process of claim 1, wherein R$^1$ is Cl.

11. A process for preparing a compound of the formula

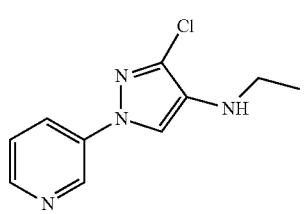

comprising
 a. contacting a compound of the formula 1b

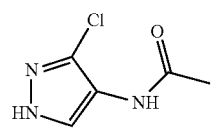

with a 3-halopyridine in the presence of a copper catalyst, a ligand, a base and an additive to provide a compound of the formula 1c b. contacting a compound of the formula 1c

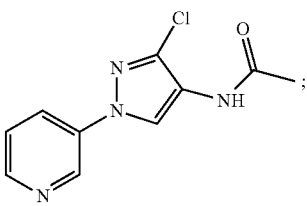 [SMILES: CC(=O)Nc1cn(-c2cccnc2)nc1Cl]

with an alkylating agent in the presence of a base to provide a compound of the formula 1c'

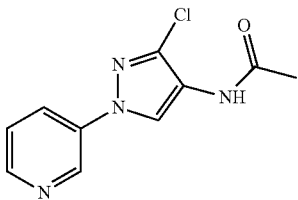 [SMILES: CC(=O)Nc1cn(-c2cccnc2)nc1Cl]

and c. contacting a compound of the formula 1c'

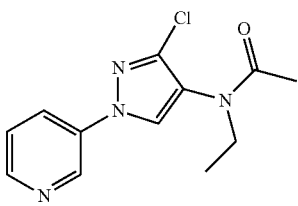 [SMILES: CCN(C(C)=O)c1cn(-c2cccnc2)nc1Cl]

with an inorganic acid to provide compound 1d.

12. The process of claim 11, wherein the copper catalyst in step (a) is copper (I) chloride (CuCl), copper (II) chloride (CuCl$_2$), copper (I) bromide (CuBr) or copper (I) iodide (CuI).

13. The process of claim 11, wherein the ligand in step (a) is selected from the group consisting of triethylenetetramine (TETA), N,N'-bis(2-hydroxyethyl)ethylenediamine (BHEEA) and 8-hydroxyquinoline.

14. The process of claim 11, wherein the additive is used in step (a), and the additive is a dialkylamine, a trialkylamine, a benzonitrile or N,N,N'N'-tetramethylethylenediamine (TMEDA).

15. The process of claim 11, wherein the ligand in step (a) is N,N'-dimethylethane-1,2-diamine (DMEDA), and the additive is used and the additive is a dialkylamine, a trialkylamine, a benzonitrile or N,N,N'N'-tetramethylethylenediamine (TMEDA).

16. The process of claim 11, wherein the base in step (a) is selected from the group consisting of sodium bicarbonate (NaHCO$_3$), sodium carbonate (Na$_2$CO$_3$), calcium carbonate (CaCO$_3$), cesium carbonate (Cs$_2$CO$_3$), lithium carbonate (Li$_2$CO$_3$), potassium carbonate (K$_2$CO$_3$), lithium hydroxide (LiOH), sodium hydroxide (NaOH), potassium hydroxide (KOH), cesium hydroxide (CsOH), calcium hydroxide (Ca(OH)$_2$), sodium diphosphate (Na$_2$HPO$_4$), potassium phosphate (K$_3$PO$_4$), sodium phosphate (Na$_3$PO$_4$), sodium methoxide (NaOCH$_3$) and sodium ethoxide (NaOCH$_2$CH$_3$).

17. The process of claim 11, wherein the solvent of step (a) is acetonitrile (CH$_3$CN), benzonitrile, dioxane, N, N-dimethylformamide (DMF), N-methyl-2-pyrrolidone (NMP), tetrahydrofuran (THF), 2-methyl tetrahydrofuran, dimethylsulfoxide (DMSO), toluene, methanol (MeOH), or ethanol (EtOH).

18. The process of claim 11, wherein the alkylating agent in step (b) is a C$_1$-C$_6$ alkyl group substituted with a leaving group selected from the group consisting of Br, I, a triflate (-OTf), a tosylate (-OTs) and a mesylate (-OMs).

19. The process of claim 11, wherein the base in step (b) is selected from the group consisting of sodium bicarbonate (NaHCO$_3$), sodium carbonate (NaHCO$_3$), calcium carbonate (CaCO$_3$), cesium carbonate (Cs$_2$CO$_3$), lithium carbonate (Li$_2$CO$_3$), potassium carbonate (K$_2$CO$_3$), lithium hydroxide (LiOH), sodium hydroxide (NaOH), potassium hydroxide (KOH), cesium hydroxide (CsOH), calcium hydroxide (Ca(OH)$_2$), sodium hydride (NaH), lithium hydride (LiH), potassium hydride (KH), sodium methoxide (NaOCH$_3$), sodium ethoxide (NaOCH$_2$CH$_3$) and sodium t-butoxide (NaOt-Bu).

20. The process of claim 11, wherein the inorganic acid in step (c) is selected from the group consisting of HF, HCl, HBr, H$_2$SO$_4$, H$_3$PO$_4$, H$_3$BO$_4$, HNO$_3$ and HClO$_4$.

* * * * *